US012685741B2

(12) United States Patent
Remmereit et al.

(10) Patent No.: US 12,685,741 B2
(45) Date of Patent: *Jul. 21, 2026

(54) N-ACETYLNEURAMINIC ACID COMPOSITIONS AND METHODS OF USE

(71) Applicant: LifeScience AS, Ørsta (NO)

(72) Inventors: Jan Remmereit, Hovdebygda (NO); Hogne Vik, Oslo (NO)

(73) Assignee: LifeScience AS, Ørsta (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/755,410

(22) PCT Filed: Oct. 11, 2018

(86) PCT No.: PCT/IB2018/001278
§ 371 (c)(1),
(2) Date: Apr. 10, 2020

(87) PCT Pub. No.: WO2019/073298
PCT Pub. Date: Apr. 18, 2019

(65) Prior Publication Data
US 2021/0220378 A1 Jul. 22, 2021

Related U.S. Application Data

(60) Provisional application No. 62/570,937, filed on Oct. 11, 2017, provisional application No. 62/613,232, filed on Jan. 3, 2018.

(51) Int. Cl.
| | |
|---|---|
| *A61K 31/7012* | (2006.01) |
| *A61K 9/00* | (2006.01) |
| *A61K 9/08* | (2006.01) |
| *A61K 47/10* | (2017.01) |
| *A61K 47/36* | (2006.01) |
| *A61M 11/00* | (2006.01) |
| *A61P 11/02* | (2006.01) |
| *A61P 31/16* | (2006.01) |

(52) U.S. Cl.
CPC ........ *A61K 31/7012* (2013.01); *A61K 9/0043* (2013.01); *A61K 9/08* (2013.01); *A61K 47/10* (2013.01); *A61K 47/36* (2013.01); *A61M 11/007* (2014.02); *A61P 11/02* (2018.01); *A61P 31/16* (2018.01); *A61M 2205/70* (2013.01); *A61M 2210/0618* (2013.01)

(58) Field of Classification Search
None
See application file for complete search history.

(56) References Cited

U.S. PATENT DOCUMENTS

| | | | | |
|---|---|---|---|---|
| 6,572,849 B2 * | 6/2003 | Shahinian, Jr. | ........ | A61K 47/12 514/23 |
| 7,122,206 B2 | 10/2006 | Kim | | |
| 8,541,003 B2 * | 9/2013 | Anderson | ............ | C12N 15/866 435/69.3 |
| 2009/0081249 A1 * | 3/2009 | Haldar | ................ | A61K 47/551 424/193.1 |
| 2010/0204314 A1 * | 8/2010 | Yamashita | ........... | C07D 309/28 514/459 |
| 2011/0085981 A1 * | 4/2011 | Wang | ................ | A61K 31/7012 506/13 |
| 2012/0282350 A1 | 11/2012 | Remmereit | | |
| 2016/0038518 A1 * | 2/2016 | Sher | ....................... | A61K 45/06 514/114 |

FOREIGN PATENT DOCUMENTS

| | | | | |
|---|---|---|---|---|
| CN | 102488697 | | 6/2012 | |
| CN | 102488697 A | * | 6/2012 | ......... A61K 31/7016 |
| EP | 0296620 | | 10/1992 | |
| WO | WO 92/14473 | | 9/1992 | |
| WO | WO 2010/052575 | | 5/2010 | |
| WO | WO 2014/151523 | | 9/2014 | |

OTHER PUBLICATIONS

Ryan, W. R., & Hwang, P. H. (2010). Safety of a preservative-free acidified saline nasal spray: a randomized, double-blind, placebo-controlled, crossover clinical trial. Archives of Otolaryngology-Head & Neck Surgery, 136(11), 1099-1103. (Year: 2010).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
International Search Report and Written Opinion for PCT/IB2018/001278. Mailed Apr. 2, 2019. 19 pages.
Bardor et al., Mechanism of uptake and incorporation of the non-human sialic acid N-glycolylneuraminic acid into human cells. J Biol Chem. Feb. 11, 2005;280(6):4228-37.
Boehm et al., Oligosaccharides from milk. J Nutr. Mar. 2007; 137(3 Suppl 2):847S-9S.
Brady et al., Treatment of herpes simplex virus infections. Antiviral Res. Feb. 2004;61(2):73-81.
Choi et al., Safety evaluation of the human-identical milk monosaccharide sialic acid (N-acetyl-d-neuraminic acid) in Sprague-Dawley rats. Regul Toxicol Pharmacol. Nov. 2014;70(2):482-91.
Cox et al., Global epidemiology of influenza: past and present. Annu Rev Med. 2000;51:407-21.
Doultree et al., InacDOULTREE et al., Inactivation of feline calicivirus, a Norwalk virus surrogate. J Hosp Infect. Jan. 1999;41(1):51-7.
GRAS Notice (GRN) No. 602. Original Submission. FDA. 2015. Retrieved from the internet Aug. 24, 2022. 83 pages.
Martín-Sosa et al., The sialylated fraction of milk oligosaccharides is partially responsible for binding to enterotoxigenic and uropathogenic *Escherichia coli* human strains. J Nutr. Oct. 2002;132(10):3067-72.
Neu et al., Viruses and sialic acids: rules of engagement. Curr Opin Struct Biol. Oct. 2011;21(5):610-8.

(Continued)

*Primary Examiner* — Dale R Miller
(74) *Attorney, Agent, or Firm* — Casimir Jones, S.C.; J. Mitchell Jones

(57) ABSTRACT

The present invention relates to the field of viral disorders, and in particular to the use of natural compounds to inhibit viruses and viral infection. Compositions comprising NANA are provided for treating or preventing viral infections, such as those causing the common cold.

7 Claims, 5 Drawing Sheets

(56)         References Cited

OTHER PUBLICATIONS

Newburg. Do the binding properties of oligosaccharides in milk protect human infants from gastrointestinal bacteria? J Nutr. May 1997;127(5 Suppl):980S-984S.

Nicolson. Considerations when undergoing treatment for chronic illnesses and autoimmune diseases. J. Medicine 1998; 1:123-128.

Ryan et al., Safety of a preservative-free acidified saline nasal spray. Arch Otolaryngol Head Neck Surg. 2010;136(11):1099-1103.

Samraj et al., A red meat-derived glycan promotes inflammation and cancer progression. Proc Natl Acad Sci U S A. Jan. 13, 2015;112(2):542-7.

Schnaars et al., Sialic acids in the brain: gangliosides and polysialic acid in nervous system development, stability, disease, and regeneration. Physiol Rev. Apr. 2014;94(2):461-518.

Shenk. Adenoviridae: The Viruses and Their Replication. Fields Virology, Third Edition, Chpt 67. Lippincott-Raven. 1996. 2111-2148.

Slomka et al., Feline calicivirus as a model system for heat inactivation studies of small round structured viruses in shellfish. Epidemiol Infect. Oct. 1998;121(2):401-7.

Sprenger et al., Sialic acid utilization. Adv Nutr. May 1, 2012;3(3):392S-7S.

Stehle et al., Rules and exceptions: sialic acid variants and their role in determining viral tropism. J Virol. Jul. 2014;88(14):7696-9.

Stencel-Baerenwald et al., The sweet spot: defining virus-sialic acid interactions. Nat Rev Microbiol. Nov. 2014;12(11):739-49.

Straub et al., In vitro cell culture infectivity assay for human noroviruses. Emerg Infect Dis. Mar. 2007;13(3):396-403.

Trappetti et al., Sialic acid: a preventable signal for pneumococcal biofilm formation, colonization, and invasion of the host. J Infect Dis. May 15, 2009;199(10):1497-505.

Urashima et al., Oligosaccharides of milk and colostrum in non-human mammals. Glycoconjugate Journal. 2001; 18: 357-371.

Varki. Sialic acids in human health and disease. Trends Mol Med. Aug. 2008;14(8):351-60.

Wang The role and potential of sialic acid in human nutrition. Eur J Clin Nutr. Nov. 2003;57(11):1351-69.

Wojtczak. Glossary of medical education terms. IIME. 2002. 5 pages.

* cited by examiner

*N*-Acetylneuraminic acid (NeuAc)

*N*-Glycolylneuraminic acid (NeuGc)

FIG. 2 a
Neu5Ac

Neu5Gc b

α2,3-linkage

α2,6-linkage

α2,8-linkage

Content of free and bound NeuSAc in certain food products. Ref Samraj et al. 10.1073/ pnas.1417508112

NeuSAc in mcg/100g food products
ref:Ref Samraj et al. 10.1073/pnas.1417508112

N-ACETYLNEURAMINIC ACID COMPOSITIONS AND METHODS OF USE

FIELD OF THE INVENTION

The present invention relates to the use of compositions comprising N-acetylneuraminic acid (sialic acid, Neu5Ac or NANA). Compositions comprising NANA find use in inducing physiological responses such as alleviating the symptoms of colds and preventing the onset of colds.

BACKGROUND OF THE INVENTION

In the course of a year, individuals in the United States suffer 1 billion colds, according to some estimates. Colds are most prevalent among children, and seem to be related to youngsters' relative lack of resistance to infection and to contacts with other children in day-care centers and schools. Children have about six to ten colds a year. In families with children in school, the number of colds per child can be as high as 12 a year. Adults average about two to four colds a year, although the range varies widely. Women, especially those aged 20 to 30 years, have more colds than men, possibly because of their closer contact with children. On average, individuals older than 60 have fewer than one cold a year.

The economic impact of the common cold is enormous. The National Center for Health Statistics (NCHS) estimates that, in 1994, 66 million cases of the common cold in the United States required medical attention or resulted in restricted activity. In 1994, colds caused 24 million days of restricted activity and 20 million days lost from school, according to NCHS.

More than 200 different viruses are known to cause the symptoms of the common cold. Some, such as the rhinoviruses, seldom produce serious illnesses. Others, such as parainfluenza and respiratory syncytial virus, produce mild infections in adults but can precipitate severe lower respiratory infections in young children. Rhinoviruses (from the Greek rhin, meaning "nose") cause an estimated 30 to 35 percent of all adult colds, and are most active in early fall, spring and summer. More than 110 distinct rhinovirus types have been identified. These agents grow best at temperatures of 33 degrees Celsius [about 91 degrees Fahrenheit (F)], the temperature of the human nasal mucosa. Coronaviruses are believed to cause a large percentage of all adult colds. They induce colds primarily in the winter and early spring. Of the more than 30 isolated strains, three or four infect humans. The importance of coronaviruses as causative agents is hard to assess because, unlike rhinoviruses, they are difficult to grow in the laboratory.

In the United States, most colds occur during the fall and winter. Beginning in late August or early September, the incidence of colds increases slowly for a few weeks and remains high until March or April, when it declines. The seasonal variation may relate to the opening of schools and to cold weather, which prompt people to spend more time indoors and increase the chances that viruses will spread from person to person.

Symptoms of the common cold usually begin two to three days after infection and often include nasal discharge, obstruction of nasal breathing, swelling of the sinus membranes, sneezing, sore throat, cough, and headache. Fever is usually slight but can climb to 102° F. in infants and young children. Cold symptoms can last from two to 14 days, but two-thirds of people recover in a week. If symptoms occur often or last much longer than two weeks, they may be the result of an allergy rather than a cold. Colds occasionally can lead to secondary bacterial infections of the middle ear or sinuses, requiring treatment with antibiotics. High fever, significantly swollen glands, severe facial pain in the sinuses, and a cough that produces mucus, may indicate a complication or more serious illness requiring a doctor's attention.

Viruses cause infection by overcoming the body's complex defense system. The body's first line of defense is mucus, produced by the membranes in the nose and throat. Mucus traps inhaled materials: pollen, dust, bacteria and viruses. When a virus penetrates the mucus and enters a cell, it commandeers the protein-making machinery to manufacture new viruses which, in turn, attack surrounding cells.

Cold symptoms are probably the result of the body's immune response to the viral invasion. Virus-infected cells in the nose send out signals that recruit specialized white blood cells to the site of the infection. In turn, these cells emit a range of immune system chemicals such as kinins. These chemicals probably lead to the symptoms of the common cold by causing swelling and inflammation of the nasal membranes, leakage of proteins and fluid from capillaries and lymph vessels, and the increased production of mucus. Kinins and other chemicals released by immune system cells in the nasal membranes are the subject of intensive research. Researchers are examining whether drugs to block them, or the receptors on cells to which they bind, might benefit people with colds.

Despite the economic and health costs associated with colds, there are very few drugs or natural compounds that have been proven to fight the viruses that cause colds. What is needed in the art are natural compounds for preventing and treating colds.

SUMMARY OF THE INVENTION

The present invention relates to the use of compositions comprising N-acetylneuraminic acid (sialic acid, Neu5Ac or NANA). Compositions comprising NANA find use in inducing physiological responses such as alleviating the symptoms of colds and preventing the onset of colds.

In some embodiments, the present invention provides compositions for treating, inhibiting, alleviating or preventing colds, or reducing symptoms associated therewith, comprising an effective concentration of NANA. In some embodiments, the compositions further comprise an excipient. In some embodiments, the compositions are formulated for oral administration. In some embodiments, the compositions are formulated as a tablet. In some embodiments, the compositions are formulated as a capsule. In some embodiments, the compositions further comprise a foodstuff. In some embodiments, the compositions are formulated as a nasal sprays for nasal administration. In some embodiments, the compositions are gels. In some embodiments, the compositions are aqueous solutions. In some embodiments, the compositions are formulated as a pump spray, aerosol spray, gel, powder, lotion, foam or cream for topical or intranasal administration. In some embodiments, the effective concentration is from about 1 nM to about 10 mM.

In some embodiments, the composition further comprises a thixotropic agent (e.g., including but not limited to, fucoidans, alginates or chitosan). In some embodiments, the thixotropic agent is mannuronic acid. In some embodiments, the mannuronic acid is present in the composition at a w/w percent range of 0.01 to 2.0% (e.g., 0.01 to 1.0% or 0.1 to 0.5%).

In some embodiments, the present invention provides methods for treating a human or animal subject comprising providing a composition comprising NANA in an effective concentration and administering said composition intranasally. In some embodiments, the composition is selected from the group consisting of gels, solutions, sprays, powders, creams, foams and lotions. In some embodiments, the effective concentration is from about 1 nM to about 10 mM.

In some embodiments, the present invention provides methods of treating, alleviating, ameliorating, reducing or inhibiting infection by a virus comprising contacting said virus with an effective concentration of NANA, wherein said virus is selected from the group consisting of influenza viruses, rhinoviruses, adenoviruses, herpes viruses and noroviruses. In some embodiments, the effective concentration is from about 1 nM to about 10 mM.

In some embodiments, the present invention provides methods of treating, alleviating, ameliorating, or inhibiting infection by a virus, or reducing symptoms or outbreaks associated with infection by the virus, comprising orally administering an effective concentration of NANA, wherein said virus is selected from the group consisting of influenza viruses, rhinoviruses, adenoviruses, herpes viruses (e.g., HSV-1 or HSV-2) and noroviruses. In some embodiments, the effective amount is from about 0.1 to 5 grams/day, and more preferably from 0.5 to 5 grams/day and most preferably from about 1 to 3 grams/day. In some embodiments, the effective amount is sufficient to reduce the frequency of herpes outbreaks in a subject infected with herpes, for example HSV-1 (Herpes Simplex Virus Type I) or HSV-2 (Herpes Simplex Virus Type I). In some embodiments, the effective amount is sufficient to inhibit or prevent herpes outbreaks in a subject infected with herpes. Herpes outbreaks can include the occurrence of sores or lesions, especially blister-like lesions, and also other lesions similar to pimples, red spots, etc. In some embodiments, the outbreak is an HSV-1 outbreak and includes lesions around the mouth, gums and nose. In some embodiments, the outbreak is an HSV-2 outbreak and includes lesions around the genital area.

In some embodiments, the present invention provides an animal feed comprising an effective concentration of NANA acid.

In some embodiments, the present invention provides a device comprising a solid support having NANA deposited thereon, wherein said device is configured to cover a body cavity on an animal or human.

In some embodiments, the present invention provides a device for administering an antiviral solution comprising a container containing a solution comprising NANA and a propellant.

In some embodiments, the present invention provides a device for administering an antiviral solution comprising NANA comprising a container containing a solution comprising NANA, a pump and a nozzle, wherein activation of said pump causes said solution comprising NANA to be expelled through said nozzle.

In some embodiments, the present invention provides a method for treating a site suspected of being contaminated by rhinovirus comprising exposing said site to a composition comprising NANA under conditions such that the percentage of viable or infectious rhinovirus is decreased. In some embodiments, the site is a surface. In some embodiments, the site is an enclosed space. In some embodiments, the enclosed space is a room. In some embodiments, the enclosed space is a vehicle. In some embodiments, the composition comprising NANA is provided as an aerosol spray. In some embodiments, the composition comprising NANA is provided as a foam.

In some preferred embodiments, the present invention provides methods for preventing, inhibiting, treating, alleviating, reducing or ameliorating ailments of the upper respiratory tract, preventing, inhibiting, treating, alleviating, reducing or ameliorating viral infection of the upper respiratory tract, reducing sick leave or days away from work due to upper respiratory infections, and/or reducing viral infection of the upper respiratory tract during public transportation, in a human or animal subject, said method comprising: intranasally administering a composition comprising N-acetylneuraminic acid (NANA) in an effective concentration to a subject under conditions such that said ailment of the upper respiratory tract is prevented, inhibited or treated; viral infection of the upper respiratory tract is inhibited or treated; sick leave or days away from work are reduced; and/or viral infection of the upper respiratory tract during public transportation is reduced. In some preferred embodiments, the ailment of the upper respiratory tract is selected from the group consisting of dryness in the nose, and development and/or presence of common colds, and rhinovirus infection.

In some preferred embodiments, the present invention provides for use of composition comprising an effective amount N-acetylneuraminic acid (NANA) to effect one or more of: preventing, inhibiting, treating, alleviating or ameliorating ailments of the upper respiratory tract, preventing, inhibiting, treating, alleviating or ameliorating viral infection of the upper respiratory tract, reducing sick leave or days away from work due to upper respiratory infections, and/or reducing viral infection of the upper respiratory tract during public transportation. In some preferred embodiments, the ailment of the upper respiratory tract is selected from the group consisting of dryness in the nose, and development and/or presence of common colds, and rhinovirus infection.

In some preferred embodiments, the effective concentration of NANA is from about 0.1 to about 10 mg/ml in an aqueous solution. In some preferred embodiments, the effective concentration of NANA is from about 0.5 to about 5 mg/ml in an aqueous solution. In some preferred embodiments, the daily dosage of NANA is from about 0.1 to 5.0 mg NANA/nostril/day. In some preferred embodiments, the daily dosage of NANA is from about 0.1 to 1.0 mg NANA/nostril/day. In some preferred embodiments, the pH of composition comprising N-acetylneuraminic acid (NANA), preferably in aqueous solution, is from 2.0 to 4.0. In some preferred embodiments, the pH of composition comprising N-acetylneuraminic acid (NANA), preferably in aqueous solution, is from 2.5 to 3.7. In some preferred embodiments, the pH of composition comprising N-acetylneuraminic acid (NANA), preferably in aqueous solution, is from 2.8 to 3.2. In some preferred embodiments, the daily dosage of NANA is delivered in from 2 to 8 administrations per day. In some preferred embodiments, the composition further comprises a thixotropic agent. In some preferred embodiments, the thixotropic agent is selected from the group consisting of fucoidans, alginates and chitosan. In some preferred embodiments, the thixotropic agent is mannuronic acid. In some preferred embodiments, the mannuronic acid is present in said composition at a w/w percent range of 0.01 to 2.0%. In some preferred embodiments, the mannuronic acid is present in said composition at a w/w percent range of 0.01 to 1.0%. In some preferred embodiments, the said mannuronic acid is present in said composition at a w/w percent range of 0.1% to 0.5%.

In some preferred embodiments, the present invention provides a composition, comprising: an aqueous solution of from 0.1 to 10 mg/ml NANA suitable for application to mucous membranes. In some preferred embodiments, the pH of composition comprising N-acetylneuraminic acid (NANA), preferably in aqueous solution, is from 2.0 to 4.0. In some preferred embodiments, the pH of composition comprising N-acetylneuraminic acid (NANA), preferably in aqueous solution, is from 2.5 to 3.7. In some preferred embodiments, the pH of composition comprising N-acetyl-neuraminic acid (NANA), preferably in aqueous solution, is from 2.8 to 3.2. In some preferred embodiments, the effective concentration of NANA is from about 0.5 to about 5 mg/ml in an aqueous solution. In some preferred embodiments, the compositions further comprise a thixotropic agent. In some preferred embodiments, the thixotropic agent is selected from the group consisting of fucoidans, alginates and chitosan. In some preferred embodiments, the thixotropic agent is mannuronic acid. In some preferred embodiments, the mannuronic acid is present in said composition at a w/w percent range of 0.01 to 2.0%. In some preferred embodiments, the mannuronic acid is present in said composition at a w/w percent range of 0.01 to 1.0%. In some preferred embodiments, the mannuronic acid is present in said composition at a w/w percent range of 0.10% to 0.5%. In some preferred embodiments, the composition is a nasal spray.

In some preferred embodiments, the present invention provides a spray bottle configured for application of a nasal spray to the nose of animal or human containing any of the compositions described above. In some preferred embodiments, the spray bottle is calibrated to deliver a spray dose comprising from 0.03 to 1.0 mg NANA/spray. In some preferred embodiments, the spray bottle is calibrated to deliver a spray dose comprising from 0.05 to 0.3 mg NANA/spray.

In some preferred embodiments, the present invention provides any of the compositions or spray bottles described above for use to treat, alleviate, inhibit, reduce the frequency of, ameliorate or prevent ailments of the upper respiratory tract, treat, alleviate, inhibit, reduce the frequency of, ameliorate or prevent viral infection of the upper respiratory tract, reduce sick leave or days away from work due to upper respiratory infections, and/or reduce viral infection of the upper respiratory tract during public transportation. In some preferred embodiments, the ailment of the upper respiratory tract is selected from the group consisting of dryness in the nose, and development and/or presence of common colds, and rhinovirus infection. In preferred embodiments, it will be understood that that the prevention, decrease, alleviation, inhibition or reduction observed is on comparison to an untreated subject.

In some preferred embodiments, the present invention provides any of the compositions or spray bottles described above for use 1) to prevent, decrease, alleviate, inhibit or reduce the frequency of dripping nose in human subjects; 2) to prevent, decrease, alleviate, inhibit or reduce the frequency of snoring in human subjects; 3) to prevent, decrease, alleviate, inhibit or reduce the frequency of clogged nasal cavities in subjects suffering chronically clogged nasal cavities; 4) to treat, alleviate or prevent chronic immune deficiency; 5) treat, alleviate, inhibit, reduce, ameliorate or prevent nephritis or glomerulonephritis. In preferred embodiments, it will be understood that that the prevention, decrease, alleviation, inhibition or reduction observed is on comparison to an untreated subject.

In some preferred embodiments, the present invention provides any of the compositions or spray bottles described above for use in treating, preventing, ameliorating or reducing herpes outbreaks in a subject infected with herpes virus. In preferred embodiments, it will be understood that that the prevention, decrease, alleviation, inhibition or reduction observed is on comparison to an untreated subject. In some preferred embodiments, the herpes virus is HSV-1 or HSV-2. In some preferred embodiments, the effective amount of NANA is a daily dosage of from 0.5 to 5 grams per day.

In some preferred embodiments, the present invention provides methods of treating, preventing, ameliorating or reducing herpes outbreaks in a subject infected with herpes virus comprising administering to the subject an effective amount of a NANA under conditions such that the incidence of herpes outbreaks experienced by the subject is reduced in frequency. In preferred embodiments, it will be understood that that the prevention, decrease, alleviation, inhibition or reduction observed is on comparison to an untreated subject. In some preferred embodiments, the herpes virus is HSV-1 or HSV-2. In some preferred embodiments, the effective amount of NANA is a daily dosage of from 0.5 to 5 grams per day.

Additional embodiments are described herein.

DESCRIPTION OF THE FIGURES

FIG. 2 shows the general structure of how the sialic acids bind to larger glycoconjugates. 3

DEFINITIONS

Figure 1:
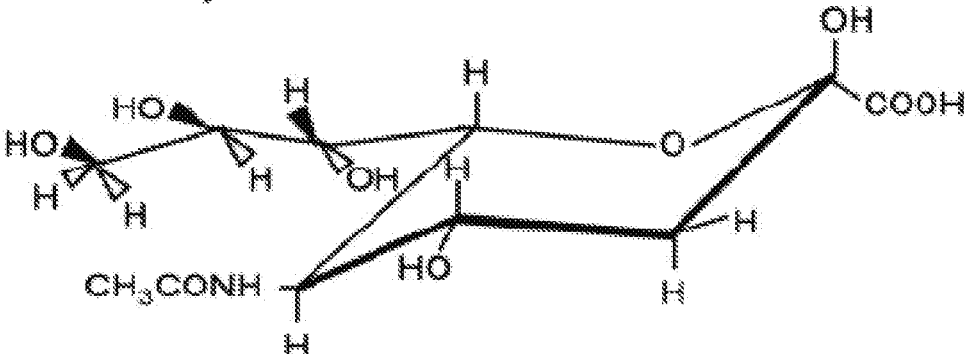
FIG. 1 shows the structure of the sialic acids N-acetyl-neuraminic acid (NANA or Neu5Ac) and N-glycolyl-neuraminic acid (Neu5Gc.)2
Figure 1:
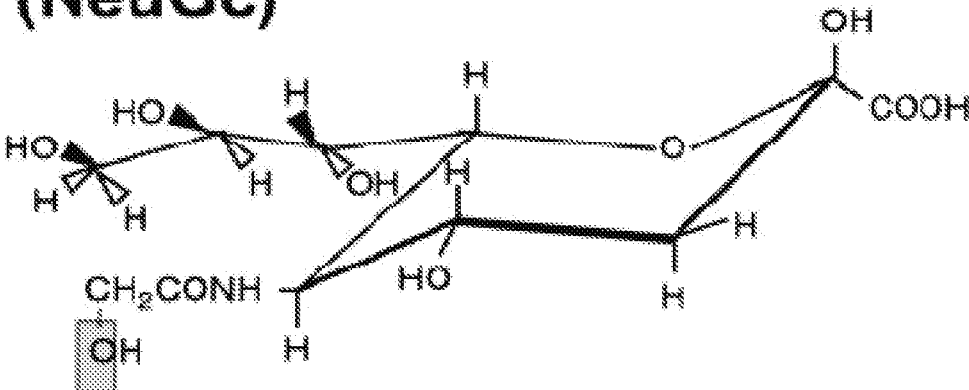

As used herein, the term "functional foods" refers to food products that include biologically active nutraceutical agents.

As used herein, the terms "nutraceutical agent," and related terms, refer to natural, bioactive chemical compounds that have health promoting, disease preventing or medicinal properties. Examples of nutraceutical agents include, but are not limited to, *Allium cepa, Allium sativum, Aloe vera, Angelica* Species, Naturally Occurring Antioxidants, *Aspergillus oryzae* Enzyme Therapy, barley grass, Bromelain, Carnitine, Carotenoids and Flavonoids, Catechin, Centella *Asiatica* (Gotu kola), Coenzyme Q10, Chinese Prepared Medicines, *Coleus forskohlii, Commiphora mukul, Crataegus oxyacantha* (Hawthorne), *Curcuma longa* (Turmeric), *Echinacea* Species (Purple Coneflower), *Eleutherococcus senticosus* (Siberian *Ginseng*), *Ephedra* Species, Dietary Fish Oil Consumption and Fish Oil Supplementation, Genistein, *Ginkgo biloba, Glycyrrhiza* (Licorice), *Hypericum perforatum* (St. John's Wort), *Hydrastis* (Goldenseal) and Other Berberine-Containing Plants, *Lactobacillus, Lobelia* (Indian Tobacco), *Melaleuca alternifolia, Mentha piperita*, NANA, *Panax ginseng*, Pancreatic Enzymes, *Piper* Mythisticum, Procyanidolic Oligomers, *Pygeum africanum*, Quercetin, *Sarsaparilla* Species, *Serenoa repens* (Saw *palmetto, Sabal serrulata*), *Silybum marianum* (Milk Thistle), Rosemary/Lemon balm, Selenite,

*Tabebuia avellanedae* (LaPacho), *Taraxacum officinale, Tanacetum parthenium* (Feverfew), Taxol, Uva *Ursi* (Bearberry), *Vaccinium myrtillus* (Blueberry), *valerian officinalis, Viscum album* (Mistletoe), Vitamin A, Beta-Carotene and Other Carotenoids, and *Zingiber officinale*(Ginger).

As used herein, the terms "subject" and "patient" refer to any animal, such as a mammal like a dog, cat, bird, livestock, and preferably a human. Specific examples of "subjects" and "patients" include, but are not limited to, individuals suffering from or at risk of the common cold (e.g., rhinovirus infection).

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

The present invention relates to the field of nutraceuticals, and in particular to nutraceuticals comprising (NANA). Compositions comprising NANA find use in inducing physiological responses such as alleviating the symptoms of colds or preventing the onset of colds.

Sialic acid is the generic name for N- or O-substituted derivatives of neuraminic acid, a monosaccharide with nine carbon atoms. The substances were first described in saliva, hence its name after the Greek word saliva: sialon. Sialic acids are found naturally in the end of the dense and complex braid of sugar molecules, proteins and lipids on cell surfaces and on many soluble proteins. Molecular, cellular and genetic studies show that sialic acids participate in the control of cell and cell matrix interactions, intermolecular interactions on cell surfaces and in interactions with other molecules in the cell's immediate extracellular environment 1.

Neu5Ac can be transformed into Neu5Gc with the enzyme CMAH (cytidine monophosphate-N-acetylneuraminic acid hydroxylase). This enzyme is not found in humans due to one deletion in the gene encoding it. One assumes therefore that man has in prehistoric times lost the functionality of this gene and thus the ability to transform NeuAc into Neu5Gc. Unlike animals and some others organisms, humans can only synthesize Neu5Ac. 2

Figure 2:
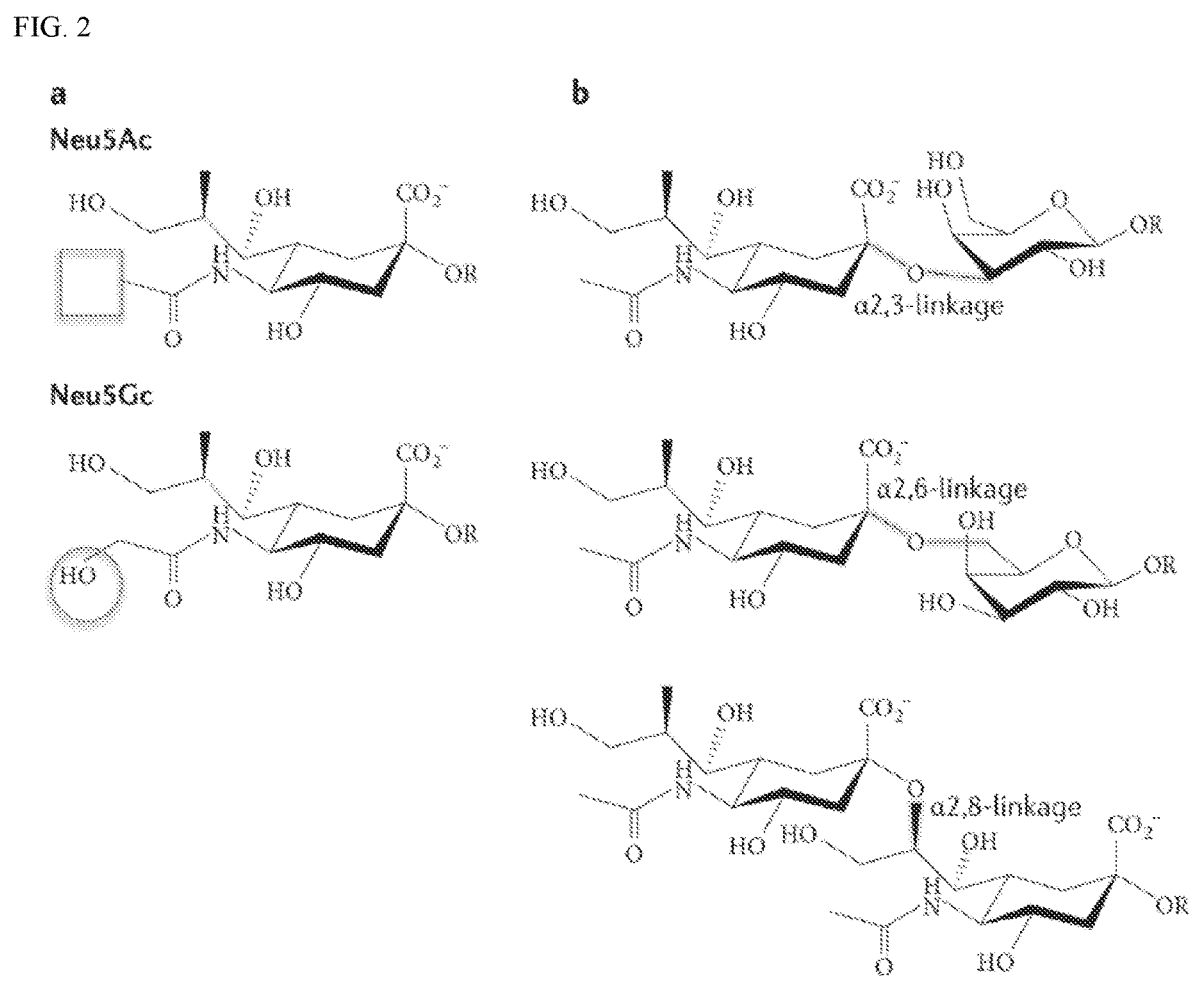

As described in detail in FIG. 2, the two most common sialic acids are N-acetyl neuraminic acid (Neu5Ac) and N-glycolylneuraminic acid (Neu5Gc) (FIG. 2*a* on the left). Carbon atom No. 5 in Neu5AC (square) can be enzymatically modified into one N-acetyl group and further hydroxylated to form Neu5Gc (circle). Hydroxyl group on several carbon atoms (C4, C7; C8 and C9) may further be modified, for example with O-acetyl, 0-sulfate, 0-lactyl, O-methyl and O-phosphate groups. The sialic acids are attached to carbohydrate chains on glycoproteins and glycolipids via different glucoside bonds. The most common bonds are $\alpha2,3$ binding to the galactose moiety, $\alpha2,6$ binding to galactose or to the N-acetylgalactosamine moiety, and $\alpha2.8$ binding to another sialic acid moiety on a glycan. Sialic acids cleave the airway epithelium—and can act as receptors for viruses. Newer research with glycan microarrays and other sophisticated methods shows the complexity of the interactions between sialic acid—containing receptors on cell surfaces and viruses proteins. This provides opportunities for studies of how viruses adhere to cell surfaces in airway epithelium 4.

According to Schalcter (2017) 5 Neu5Ac is rapidly absorbed after ingestion. It is also quickly excreted via urine. The highest concentration of sialic acids is found in saliva, urine and human brain.

The unique structure of Neu5Ac provides a molecule that has several important functionalities groups: carboxyl; hydroxyl; N-acetyl; and glycerol functions. These groups provide numerous possibilities for hydrogen bonds, salt bridges and non-polar interactions compared with monosaccharides (Schnaars et al 2014). For viruses that are able to multiply and create an infection, viruses should not just stick to epithelial surface, but also enzymatically penetrate the cell to use the cell's own replication machinery. Furthermore, new viral particles may come out of the cell. The "opening" of cell membranes can occur via a neuraminidase—an enzyme that cleaves sialic acid from glycoconjugates. The virus enzyme thus provides for additional spread of new viral particles. Studies have shown that they will also be able to neutralize silicic acid-containing soluble proteins, which will otherwise interfere with surface bonding viruses 6, 7.

It is contemplated that the supply of sialic acids can cleanse and possibly also block binding of virus to cell surfaces so that virus replication is inhibited. Studies show that sialic acids must be bound to glycoconjugates to enable them to function as receptors for virus particles. In order for this to happen, the sialic acid must first be picked up in the cell via pinocytosis—for both to be activated in the nucleus and further conjugated in Golgi apparatus conjugates transported on cell surfaces 8.

Neu et al (2011) argues that despite the binding proteins on the virus surface of different virus, and the fact that different virus types show a large variation in structure, interactions between these and the sialic acids on the host cell show astonishing similarities. This is because of how special carboxyl groups and the N-acetyl nitrogen atom on the sialic acid conjugates are oriented in space—something different from other monosaccharides. The host cell receptor surface is therefore able to bind many different viruses—both an advantage and one disadvantage to the organism.

It has long been known that breast milk has the ability to protect the infant from infections 9. Human breast milk has a high content of complex oligosaccharides with both conjugated and free sialic acid 10. Studies of human breast milk show that complex oligosaccharides-which include sialic acid—can act as soluble receptors blocking the adhesion of bacteria to cell surfaces 11. Martin-Sosa (2002) 12 showed that if such oligosaccharides lose sialic acids they do not block binding of *E coli* to the intestinal epithelium as effectively as when sialic acid is present.

If not only oligosaccharides but also soluble sialic acid can block multifunctional receptors (with regard to different virus types), therefore, it is contemplated that sialic acid can inhibit viral infection, or alternatively subsequent bacterial infection. In the case of externally administered sialic acid, excess sialic acid may be present in the epithelium capture/complex virus particles so that they do not reach the cell surface, or act as a fake receptor. Nonconjugated sialic acid may alternatively inhibit virus enzyme—neuraminidase—which opens the cell surface for effective virus replication inside the host cell. However, the present invention is not limited to a particular mechanism.

Dry nasal mucosa is often a problem that has been shown to maintain moisture better using sialic acid. This may be due to the mucus layer that is added to sialic acid becomes moister because the sialic acid with its multiple with several functional groups has a large ability to bind water via hydrogen bonds.

Despite many decades of research there are still relatively few effective anti-viral compounds in comparison to the human disease burden inflicted by viruses. Coupled with the high mutation rate of certain viruses, which enable anti-viral resistant mutants to arise with alarming speed and frequency, the need for a generic anti-viral agent is as important now as it ever has been.

Accordingly, provided herein are compositions comprising NANA for use in treating or preventing the common cold and other viral infections.

Human Rhinoviruses (HRV) are a member of the Picornaviridae. There have been more than 100 different serotypes identified to date. This diverse family of viruses is thought to be responsible for more than 80% of upper respiratory tract infections (Heikkinen & Jarvinen, 2003). As the predominant cause of the common cold, Rhinoviruses are a major human pathogen both in terms of the disease they cause and the economic impact on society.

Influenza has been established as a serious human affliction that can cause localized epidemics and global pandemics of acute respiratory infections. Each year the Influenza virus is responsible for 20,000 to 40,000 deaths and up to 300,000 hospitalization cases in the United States (Sandhu & Mossad, 2001). In the pandemic of 1918 it is widely believed that in excess of 40 million people died. Although children and younger adults experience more cases of infection, severe illness is more common in the elderly, immunocompromised individuals, or those with chronic illnesses such as asthma, diabetes, kidney failure and heart disease. The annual epidemics run from November to March in the Northern Hemisphere, and from April to September in the Southern Hemisphere (Cox N. J & Subbarao K, 2000).

The two classes of Influenza viruses that are responsible for significant human disease are termed Influenza A and Influenza B viruses. Influenza B viruses are thought to only infect humans whereas Influenza A viruses are known to infect a wide variety of animal species. Both are responsible for seasonal epidemics and, as such, are included in the annual influenza vaccines.

Herpes Simplex Virus type 1 (HSV-1) is a member of Herpesviridae, which causes infections in humans. HSV-1 has a worldwide distribution with an estimated 60-95% of the adult population infected (Brady, R. C. & Bernstein, D.

I., 2004). HSV-1 is frequently associated with oral disease, normally resulting in the formation of facial lesions. This is an important neurotropic virus which can infect the central nervous system (Immergluck et al., 1998). Once access is gained by the virus to the neurons in sensory ganglia a latent infection can be established (Kramer et al., 2003). Very little is known about the biological processes involved, but under certain stress conditions reactivation is triggered, typically resulting in the reemergence of the external lesions (Itzhaki & Lin, 1998; Qiu and Abdel-Meguid 1999). Herpes Simplex Virus type 2 (HSV-2) is a member of Herpesviridae, which causes genital infections in humans.

Adenoviruses are a group of viruses which cause a wide range of diseases. They are known to infect the lining of the eyes, the respiratory tract, the intestines, and the urinary tract and are also one of the causative agents of common cold symptoms. The virus can be split into six sub-groups from A to F based on biological and antigenic characteristics (Horwitz, 1996; Shenk 1996). Treatment advice for adenovirus infection is usually bed rest and associated with the treatment of the symptoms, as at present there is no effective specific antiviral for this virus.

Noroviruses are the most common cause of viral gastroenteritis (Caul et al., 1993; Hedberg & Osterholm, 1993). Consequently, Norovirus is sometimes known as the 'winter vomiting virus' because it is more evident during the winter period. The virus is extremely contagious and is found in the vomit and faeces of infected individuals. Currently, Noroviruses cannot be grown in the laboratory by conventional means. However, in the last year some progress has been made on propagation techniques that involve the use of bioreactors with small intestinal epithelial cells (Straub et al., 2007). However, currently, it is necessary to use a surrogate virus to test the potential virucidal effects against Noroviruses. The most established of the surrogate Norovirus viruses is the Feline Calicivirus, which like Norovirus, belongs to the Caliciviridae family of viruses (Slomka et al., 1998; Doultree et al., 1999).

In some preferred embodiments, the present invention provides NANA compositions methods of using NANA compositions for the prevention and/or treatment of viral infections caused by members of the following families of viruses: Picornaviridae, Caliciviridae, Adenoviridae, Herpesviridae, and Orthomyxoviridae, and in particular common colds caused by rhinoviruses.

Exemplary formulations are described in detail below. However, in some embodiments, NANA is formulated as a lotion, spray, gel, ointment, powder, aqueous or non-aqueous solution for topical, intranasal, intravaginal, intraanal, or sublingual administration; as a capsule, powder, or tablet for enteral administration; or as a solution for parenteral administration.

NANA compositions of the present invention may be delivered in any suitable format. In some embodiments, the NANA is preferably about greater than 90%, 95%, 99% or 99.9% pure. In some embodiments, the NANA is HPLC purified. For example, NANA can be purchased commercially from, for example, Sigma Chemical Company, St. Louis, MO. In some embodiments, the present invention provides methods of treating, alleviating, ameliorating, or inhibiting infection by a virus, or reducing symptoms or outbreaks associated with infection by the virus, comprising orally administering an effective concentration of NANA, wherein said virus is selected from the group consisting of influenza viruses, rhinoviruses, adenoviruses, herpes viruses and noroviruses. In some embodiments, the effective amount is from about 0.1 to 5 grams/day, and more preferably from 0.5 to 5 grams/day and most preferably from about 1 to 3 grams/day. In some embodiments, the effective amount is sufficient to reduce the frequency of herpes outbreaks in a subject infected with herpes. In some embodiments, the effective amount is sufficient to inhibit or prevent herpes outbreaks in a subject infected with herpes. Herpes outbreaks can include the occurrence of sores or lesions, especially blister-like lesions, and also other lesions similar to pimples, red spots, etc. In some embodiments, the outbreak is an HSV-1 outbreak and includes lesions around the mouth, gums and nose. In some embodiments, the outbreak is an HSV-2 outbreak and includes lesions around the genital area.

In some preferred embodiments, an effective concentration of NANA is from about 0.1 to about 10 mg/ml in an aqueous solution, for example, for treating, alleviating, ameliorating, reducing or inhibiting infection by rhinovirus or influenza virus or symptoms associated with rhinovirus or influenza virus infection. In some preferred embodiments, the effective concentration of NANA is from about 0.5 to about 5 mg/ml in an aqueous solution. In some preferred embodiments, the daily dosage of NANA is from about 0.1 to 5.0 mg NANA/nostril/day. In some preferred embodiments, the daily dosage of NANA is from about 0.1 to 1.0 mg NANA/nostril/day. In some preferred embodiments, the pH of composition comprising N-acetylneuraminic acid (NANA), preferably in aqueous solution, is from 2.0 to 4.0. In some preferred embodiments, the pH of composition comprising N-acetylneuraminic acid (NANA), preferably in aqueous solution, is from 2.5 to 3.7. In some preferred embodiments, the pH of composition comprising N-acetylneuraminic acid (NANA), preferably in aqueous solution, is from 2.8 to 3.2.

In some embodiments, the NANA compositions are provided in an aqueous solution, including gels, suitable for use as a spray or mist. In some embodiments, the aqueous NANA solution is incorporated into a pump-spray container, such as precompression pump, or a device such as a nebulizer or cold mist system, for delivery into the nose, mouth or lungs as a fine mist or spray. In some preferred embodiments, the present invention provides a spray bottle configured for application of a nasal spray to the nose of animal or human containing any of the compositions described above. In some preferred embodiments, the daily dosage of NANA is from about 0.1 to 5.0 mg NANA/nostril/day. In some preferred embodiments, the daily dosage of NANA is from about 0.1 to 1.0 mg NANA/nostril/day. In some preferred embodiments, the spray bottle is calibrated to deliver a spray dose comprising from 0.03 to 1.0 mg NANA/spray. In some preferred embodiments, the spray bottle is calibrated to deliver a spray dose comprising from 0.05 to 0.3 mg NANA/spray. In some preferred embodiments, the daily dosage of NANA is delivered in from 2 to 8 administrations per day from the spray bottle, i.e., from 2 to 8 pumps of the spray to each nostril.

In some embodiments, the composition further comprises a thixotropic agent (e.g., including but not limited to, fucoidans, alginates or chitosan). In some embodiments, the thixotropic agent is mannuronic acid. In some embodiments, the mannuronic acid is present in the composition at a w/w percent range of 0.01 to 2.0% (e.g., 0.01 to 1.0% or 0.1% to 0.5%).

In some embodiments, the NANA compositions of the present invention contain a pharmaceutically acceptable excipient which is effective in forming a thixotropic suspension of the solid particles of medicament comprising the composition, such as those described in U.S. Pat. No.

7,122,206. The excipient is preferably present in an amount which maintains the particles of medicament suspended in the composition during non-use and during spray of the composition into the nasal cavity, and also when the composition is deposited on the mucosal surfaces of the nasal cavities or endothelial surfaces in the nasal cavity or elsewhere in the body. In some embodiments, the viscosity of the composition at rest is relatively high, for example, about 400 to about 1000 cp. As the composition is subjected to shear forces, for example, upon being subjected to forces involved in its being agitated before spraying, the viscosity of the composition decreases (for example, to about 50 to about 200 cp) and it flows readily through the spray device and exits therefrom in the form of a fine plume which infiltrates and deposits on the mucosal surfaces of at least the following parts of the nose: the anterior regions of the nose (frontal nasal cavities); the frontal sinus; the maxillary sinuses; and the turbinates which overlie the conchas of the nasal cavities. Thus, the NANA compositions comprise a freely flowable liquid, and in sprayed form, a fine mist that finds its way to and deposits on the desired mucosa. In deposited and relatively unstressed form, the composition increases in viscosity and assumes its gel-like form which includes particles of the medicament suspended therein and which resists being cleared from the nasal passages by the inherent mucocillary forces that are present in the nasal cavities.

Any pharmaceutically acceptable material which is capable of maintaining the solid particles of medicament dispersed substantially uniformly in the composition and of imparting to the composition desired thixotropic properties can be used. Such material is referred to as a "suspending agent". Examples of suspending agents include carboxymethylcellulose, veegum, tragacanth, bentonite, methylcellulose, and polyethylene glycols. A preferred suspending agent is a mixture of microcrystalline cellulose and carboxymethylcellulose, the former being present preferably in a major amount, most preferably in an amount of about 85 to about 95 wt. %, with the latter constituent comprising about 5 to about 15 wt. % of the mixture.

The amount of suspending agent comprising the composition will vary depending on the particular medicament and amount used, the particular suspending agent used, the nature and amounts of the other ingredients comprising the composition, and the particular viscosity values that are desired. Generally speaking, it is believed that the most widely used compositions will comprise about 1 to about 5 wt. % of the suspending agent.

The NANA compositions of the present invention includes preferably other ingredients which impart desired properties to the composition. In some embodiments, dispersing or wetting agents are utilized. Any dispersing agent which is effective in wetting the particles and which is pharmaceutically acceptable can be used. Examples of dispersing agents that can be used are fatty alcohols, esters, and ethers, including, for example, those sold under the trademarks Pluronic, Tergitol, Span, and Tween. It is preferred to use a hydrophilic, non-ionic surfactant. Excellent results have been achieved utilizing sorbitan monooleatepolyoxyethylene which is available under the trademark Polysorbate 80.

In some embodiments, the compositions comprise an anti-oxidant. Examples of pharmaceutically acceptable anti-oxidants that can be used in the composition include ascorbic acid, sodium ascorbate, sodium bisulfite, sodium thiosulfate, 8-hydroxy quinoline, and N-acetyl cysterine. It is recommended that the composition comprise about 0.001 to about 0.01 wt. % of the anti-oxidant.

Also, for stability purposes, the NANA compositions should be protected from microbial contamination and growth. Examples of pharmaceutically acceptable anti-microbial agents that can be used in the composition include quaternary ammonium compounds, for example, benzalkonium chloride, benzethonium chloride, cetrimide, and cetylpyridinium chloride; mercurial agents, for example, phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other anti-microbial agents such as chlorhexidine, chlorocresol, and polymyxin. It is recommended that the composition comprise about 0.001 to about 1 wt. % of the anti-microbial agent.

As mentioned above, an aspect of the present invention comprises a composition which is odorless and which contains a mixture of stabilizing agents which function as an anti-oxidant and as an anti-microbial agent. The mixture comprises a quaternary ammonium compound that has antimicrobial properties and a material which is generally recognized as a chelating agent. The use in the composition of this combination of materials with the medicament, for example, triamcinolone acetonide, results in a highly stable composition that is resistant to oxidative degradation and to the growth of bacteria and the like. In preferred form, the mixture comprises benzalkonium chloride and disodium ethylenediamine tetraacetate.

The odorless composition generally will comprise about 0.004 to about 0.02 wt. % of the quaternary ammonium compound and about 0.01 to about 0.5 wt. % of the chelating agent. By virtue of the use of the aforementioned mixture of compounds, it is not necessary to include in the composition a material which is considered an anti-oxidant.

The composition of the present invention includes preferably an iso-osmotic agent which functions to prevent irritation of nasal mucosa by the composition. Dextrose in anhydrous form is a preferred iso-osmotic agent. Examples of other pharmaceutically acceptable iso-osmotic agents which can be used include sodium chloride, dextrose and calcium chloride. It is recommended that the composition comprise up to about 5 wt. % of the iso-osmotic agent.

The pH of the NANA compositions will vary depending on the particular medicament used and taking into account biological acceptance and the stability of the medicament. Typically, the pH of the composition will fall within the range of about 4.5 to about 7.5. The preferred pH for a composition which contains triamcinolone acetonide is about 4.5 to about 6, most preferably about 5. Examples of pharmaceutically acceptable materials which can be used to adjust the pH of the composition include hydrochloric acid and sodium hydroxide.

The NANA compositions of the present invention can be prepared in any suitable way. In preferred form, an aqueous suspension of the solid particles of medicament and dispersing agent is formed and combined with an aqueous suspension which contains the suspending agent. The former is preferably prepared by adding the medicament to an aqueous solution of the dispersing agent and mixing thoroughly. The latter is prepared by acidifying the water (pH about 4.7 to about 5.3) prior to adding the suspending agent. In particularly preferred form, an aqueous solution of the quaternary compound (anti-microbial agent) is added to the aqueous suspension of medicament, and the other ingredients (for example, iso-osmotic agent, anti-oxidant or chelating agent) are added to the thixotropic suspension. Each of the aforementioned batches of composition is mixed thoroughly before being combined. The preferred means of combining the batches of composition is to introduce one of the batches, preferably the "medicament" batch into the bottom of the other batch, for example, by pumping the batch upwardly through the other batch. The composition comprising the combined batches is mixed thoroughly. Use of the preferred method of preparation provides an efficient and effective way for formulating a composition that has the solid particles of medicament substantially uniformly dispersed therein while avoiding problems that are generally associated with the preparation of water-based pharmaceutical compositions, for example, excessive foaming and non-uniformity of the particle dispersement.

The amount of NANA applied to each of the nasal passages will vary depending on the nature of the condition being treated and the nature of the individual being treated. In some preferred embodiments, the effective concentration of NANA is from about 0.1 to about 10 mg/ml in an aqueous solution. In some preferred embodiments, the effective concentration of NANA is from about 0.5 to about 5 mg/ml in an aqueous solution. In some preferred embodiments, the daily dosage of NANA is from about 0.001 to 0.1 mg NANA/nostril/day. In some preferred embodiments, the daily dosage of NANA is from about 0.01 to 0.05 mg NANA/nostril/day. In some preferred embodiments, the daily dosage of NANA is delivered in from 2 to 8 administrations per day.

Accordingly, the present invention provides an article of manufacture comprising a spray bottle having an NANA solution or powder therein for delivery into a body cavity such as the nose. The spray bottle may preferably comprise a pump system for expelling the NANA composition from the bottle, such as a compression mump, spray pump or precompression pump. In some preferred embodiments, the spray bottle is calibrated to deliver a spray dose comprising from 0.001 to 0.02 mg NANA/spray. In some preferred embodiments, the spray bottle is calibrated to deliver a spray dose comprising from 0.004 to 0.01 mg NANA/spray.

In some embodiments, the present invention provides an article of manufacture that is a device that can be worn over a body cavity such as the mouth or nose of an individual. In some embodiments, the device is mask, such as a surgical mask. In preferred embodiments, the mask comprises a solid support or matrix, such as a polymer matrix or a woven fabric matrix, into which an NANA composition is incorporated. In some embodiments, the NANA composition is spray coated onto the matrix as an aqueous solution, gel or powder. In some embodiments, when a breath is taken through the mask, viruses are inactivated as they contact the mask. In some embodiments, the matrix is coated with an NANA composition to provide from about 0.01 microgram to about 100 milligram NANA per $cm^2$ of the matrix, preferably from about 1 microgram to about 1 milligram NANA per $cm^2$.

In some embodiments, NANA is formulated for oral delivery. The ingredients of the supplements of this invention are preferably contained in acceptable excipients and/or carriers for oral consumption. The actual form of the carrier, and thus, the supplement itself, is not critical. The carrier may be a liquid, gel, gelcap, capsule, powder, solid tablet (coated or non-coated), tea, or the like. The supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, PA).

In some embodiments, the oral delivery vehicles described above are formulated so as to provide a daily dose of between 0.1 g and 10.0 g of NANA, preferably between 0.5 and 2.0 g of NANA, and even more preferably approximately 1.0 g of NANA. In some embodiments, an effective amount of NANA is the amount needed to inhibit the growth and proliferation of a virus of interest or to inactivate the virus. In some embodiments, the effective amount is the amount of NANA sufficient to provide a concentration of NANA of from about 1 nanomolar to 10 micromolar at a site of interest, such as the circulating bloodstream or in a body cavity such as the nasal passages or sinuses.

In some embodiments, NANA is provided in a fluid that can be used for atmospheric treatment, such as by a mist. In some embodiments, the present invention provides a device comprising a reservoir, a pump, and a nozzle, wherein the reservoir comprises a fluid comprising NANA that can be expelled via the pump through the nozzle to provide a mist comprising NANA. In some embodiments, the device is a humidifier, while in other embodiments, the device is an automated mist dispenser. In some embodiments, the NANA is provided as an aerosol spray in an appropriate aerosol spray dispensing device. Accordingly, in some embodiments, the present invention provides a device or composition comprising a NANA and an aerosol propellant. Propellants include, but are not limited to, mixtures of volatile hydrocarbons, typically propane, n-butane and isobutene, dimethyl ether (DME), methyl ethyl ether, nitrous oxide, carbon dioxide and hydrofluoroalkanes (HFA): either HFA 134a (1,1,1,2,-tetrafluoroethane) or HFA 227 (1,1,1,2,3,3,3-heptafluoropropane) or combinations of the two. Typically, the NANA fluid will be miscible with the propellant. The NANA fluid may preferably be formulated to be an aerosol mist, foaming gel, cream or lotion.

Modern aerosol spray products have three major parts; the can, the valve and the actuator or button. The can is most commonly lacquered tinplate (steel with a layer of tin) and may be made of 2 or 3 pieces of metal crimped together. Aluminum cans are also common and are generally used for more expensive products. The valve is crimped to the rig of the can, the design of this component is important in determining the spray rate. The actuator is depressed by the user to open the valve; the shape and size of the nozzle in the actuator controls the spread of the aerosol spray.

In some embodiments, the devices of the present invention comprise a piston barrier system. Packaging that uses a piston barrier system is often used for highly viscous products such as post-foaming gels, thick creams and lotions. The main benefit of the piston barrier system is that is assures separation of the product from the propellant, maintaining the purity and integrity of the formulation throughout its consumer lifespan. The piston barrier system also provides a controlled and uniform product discharge rate with minimal product retention and is economical.

In some embodiments, the devices of the present invention comprise a bag-in-can system (or BOV "bag on valve"). This system separates the product from the pressurizing agent with a hermetically-sealed, multi-layered laminated pouch, which maintains complete formulation integrity so only pure product is dispensed. In this embodiment, the NANA fluid is provided in the bag. Among its many benefits, the bag-in-can system extends a product's shelf life. Other advantages include all-attitude (360-degree) dispensing, quiet and non-chilling discharge.

These devices find use in setting where an antiviral spray, foam, gel or other fluid is needed. For example, the devices find use in dispensing an antiviral mist to treat a desired environment or space, such as a room in a building such as an office, kitchen, cubicle or lavatory, or a vehicle such a train car, airplane, bus, or taxi, van or car, or animal confinement facilities such as barns, abattoirs, poultry houses, etc. The devices can also be used to dispense NANA containing fluids on a surface such as a countertop, floor, shower, etc. In some embodiments, the devices are used to inject the NANA-containing mist into the ventilation system of a building, barn, or vehicle.

In still further embodiments, the present invention provides NANA compositions that comprise NANA in a solution, such as a normal saline solution, that can be applied to the eye. Accordingly, in some embodiments, the present invention provides an article of manufacture comprising a container equipped with a nozzle to provide drops of an NANA solution to the eye. It is contemplated that in addition to effects in the eye and surrounding tissue, NANA administration via the eye and tear channel will directly access the sinuses and associated cavities. Thus, administration of NANA and/or additional antimicrobials or antivirals in eyedrops is an effective method of administration of NANA or other compounds for the treatment of eye infections, sinus infections, and systemic treatment via the eye and tear channel, and sinuses, mucus internal surfaces for effective adsorption providing local and systemic treatments.

In other embodiments, the NANA is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

In some embodiments, the NANA is provided in water that is supplied to farm animals, such as poultry, cattle, swine, sheep and the like, or used in water used in fisheries. In other embodiments, NANA is provided in tap water or water bottles water for human use.

The NANA compositions may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the compositions of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the compositions further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D₃; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

The present invention provides dietary supplements comprising nutraceutical agents, preferably NANA either by itself or in combination with one or more additional nutraceuticals agents. Nutraceutical agents are natural, bioactive chemical compounds that have health promoting, disease preventing or medicinal properties. Examples of nutraceuticals include, but are not limited to, *Allium cepa, Allium sativum, Aloe vera, Angelica* Species, Naturally Occurring Antioxidants, *Aspergillus oryzae* Enzyme Therapy, barley grass, Bromelain, Carnitine, Carotenoids and Flavonoids, Catechin, Centella *Asiatica* (Gotu kola), Coenzyme Q10, Chinese Prepared Medicines, *Coleus forskohlii, Commiphora mukul*, Conjugated Linoleic Acids (CLAs), *Crataegus oxyacantha* (Hawthorne), *Curcuma longa* (Turmeric), *Echinacea* Species (Purple Coneflower), *Eleutherococcus senticosus* (Siberian *Ginseng*), *Ephedra* Species, Dietary Fish Oil Consumption and Fish Oil Supplementation, Genistein, *Ginkgo biloba, Glycyrrhiza* (Licorice), *Hypericum perforatum* (St. John's Wort), *Hydrastis* (Goldenseal) and Other Berberine-Containing Plants, *Lactobacillus, Lobelia* (Indian Tobacco), *Melaleuca alternifolia*, Menaquinone, *Mentha piperita, Panax ginseng*, Pancreatic Enzymes, *Piper* Mythisticum, Procyanidolic Oligomers, *Pygeum africanum*, Quercetin, *Sarsaparilla* Species, *Serenoa repens* (Saw *palmetto, Sabal serrulata*), *Silybum Marianum* (Milk Thistle), Rosemary/Lemon balm, Selenite, *Tabebuia avellanedae* (LaPacho), *Taraxacum officinale, Tanacetum parthenium* (Fewfew), Taxol, Uva *Ursi* (Bearberry), *Vaccinium myrtillus* (Blueberry), *valerian officinalis, Viscum album* (Mistletoe), Vitamin A, Beta-Carotene and Other Carotenoids, and *Zingiber officinale*(Ginger).

Several nutraceutical agents are used in treating viral disorders (e.g., Genistein (in soy/red clover), rosemary/lemon balm, selenite, barley grass, lauric acid, *Phyllanthus amarus/niruri* (see, e.g., Nicolson, G. (1998) J. Medicine 1:123-128; herein incorporated by reference in its entirety). Additional anti viral nutraceutical agents include, but are not limited to, catechins, flavanoids, *Echinacea*, cascara, and NANA.

In preferred embodiments, the present invention provides compositions comprising dietary supplements (e.g., NANA) for inducing physiological responses such as alleviating or treating the symptoms of colds, preventing the onset of colds, increasing energy and increasing the feeling of well-being in subjects. Such compositions may contain, for example, between 0.1 g and 10.0 g of dietary supplements (e.g., NANA), preferably between 0.5 g and 2.0 g of dietary supplements (e.g., NANA), and even more preferably, approximately 1.0 g of dietary supplements (e.g., NANA). Furthermore, dietary supplements (e.g., NANA) are preferably provided in an amount sufficient to induce the physiological response desired (e.g., alleviation of the symptoms of colds, prevention of the onset of colds). In some embodiments, the compositions are provided for use in inducing one of the foregoing responses, while in other embodiments, the compositions are provided for use in inducing two or more of the foregoing responses.

The present invention further provides methods for treating the physiological conditions discussed above (e.g., colds, etc.).

The dietary supplements of the present invention may further be administered in any form (e.g., pill, food product, etc.). In preferred embodiments, the dietary supplements are provided as a beverage, bar, powder, pill, or shake (e.g., a nutritional supplement as described in more detail below).

The dietary supplements of the present invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., approximately 1 g of a nutraceutical agent) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals. In preferred embodiments, a dietary supplement increases satiety and results in a decrease in caloric intake and subsequent weight loss. In particularly preferred embodiments, a dietary supplement regulates viruses (e.g., adenoviruses).

In other embodiments, the present invention provides nutritional supplements (e.g., energy bars or meal replacement bars or beverages) comprising NANA. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, eighth edition, Lea & Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the nutritional supplement preferably contain between 0.1 g and 10.0 g of NANA, preferably between 0.5 and 2.0 g NANA, and even more preferably approximately 1.0 g NANA. It is understood by those of skill in the art that other ingredients can be added to those described herein, for example, fillers, emulsifiers, preservatives, etc. for the processing or manufacture of a nutritional supplement.

In still further embodiments, the present invention provides functional foods, including food products, prepared food products, or foodstuffs comprising nutraceutical agents. For example, in some embodiments, beverages and solid or semi-solid foods comprising nutraceutical agents are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

Servings of the food product preferably contain between 0.1 g and 10.0 g of NANA, preferably between 0.5 and 2.0 g of NANA, and even more preferably approximately 1.0 g of NANA.

In some embodiments, the present invention contemplates administration of NANA to animals other than human (or to humans as described above). Preferred animals include, but are not limited, poultry, fish, companion animals such as dogs and cats, horses, swine, and ruminants such as cattle and sheep. The NANA may be administered for any of the purposes described above, e.g., prevention of viral infection, treatment of viral infections, etc. In some preferred embodiments, the present invention provides NANA compositions methods of using NANA compositions for use in animals for the prevention and/or treatment of viral infections caused by members of the following families of viruses: Picornaviridae, Caliciviridae, Adenoviridae, Herpesviridae, and Orthomyxoviridae. Exemplary formulations are described in detail above. However, in some embodiments, NANA is formulated as a lotion, spray, gel, ointment, powder, aqueous or non-aqueous solution for topical, intranasal, intravaginal, intraanal, or sublingual administration; as a capsule, powder, or tablet for enteral administration; or as a solution for parenteral administration. In some embodiments, the NANA is preferably provided as a component of a powder that can be dissolved in a water supply for animals, or used to bathe animals. In some embodiments, the NANA is provided as a liquid that can be aerosolized or misted into a barn or other enclosure containing animals. In other embodiments, the NANA is supplied as a solution that can be injected into a water system designed for animals.

In some embodiments, the present invention provides animal feeds comprising NANA. The animal feeds are preferably formulated as in known in the art. Exemplary animal feeds include diets formulated for poultry, fish, companion animals such as dogs and cats, horses, swine, and ruminants such as cattle and sheep. In some embodiments, the NANA is provided as a supplement that can be incorporated into animal feeds as they are being mixed or manufactured. In preferred embodiments, the feeds are formulated so as to provide a daily dose of between 0.1 g and 10.0 g of NANA, preferably between 0.5 and 2.0 g of NANA, and even more preferably approximately 1.0 g of NANA.

EXAMPLES

Example 1

Over a long period of time (about 10 years), some individuals—as part of their research with sialic acid occasionally used a pilot version of a sialic acid-containing nasal spray. To their surprise, the use of this spray has led to less colds and/or less severe cold symptoms.

Ease of use of the product VIIRAL Nasal spray was tested in 2017 over an 8 week period in 10 Norwegian families—each consisting of 4 members; two adults and two children or teens. During the test period, two test subjects (one adult and one child) used VIIRAL nasal spray (twice per day; two sprays per nostrils each time); while two people (one adult and one child/adolescent) did not receive any type of nasal spray or other anti-icing remedies. There were weekly registered potential side effects, taste, odor, design and use of the spray bottle, and if any of the uses were available Impact on any subjective cold symptoms.

The test confirmed that the spray bottle worked as expected, without taste and smell or others unfortunate effects. The test further confirmed that the product was safe to use and easy to manage. The test also provided data that showed a trend for regular use of VIIRAL Nasal spray over the current period (mid January-mid March) contributed to a reduction in incidents of tight nose and upper airway discomfort—seen in relation to the test "Placebo group" in each of the families—and who did not use any type of nasal spray or other relevant treatment over the 8-week test period.

Example 2

A larger group of healthy volunteers is tested in one blinded randomized placebo controlled setup. It is determined if short term use (4 weeks) of VIIRAL Nasalspray—containing the sialic acid Neu5Ac has a preventative effect on potential ailments especially in the upper respiratory tract. These ailments are dryness in the nose, and development/presence of colds. The population that is included is volunteers in a professional staff of the SAS airline's cabin crew.

Cabin crew work in a more or less "closed room" during the flights. The personnel come in close contact with and are exposed to irritants, bacteria and viruses from people from different geographical areas with different backgrounds and health status. They are also subject to time differences, large variations in temperature, air pollution, changed day rhythms and different atmospheric pressures. Cabin staff can therefore be said to have a particularly exposed workplace in view of respiratory exposure.

Participants are asked to provide weekly feedback on a set of own observations that are graded on a scale from 0-10. Participants are asked to use the whole scale to better differentiate the response options.

The hypothesis is that VIIRAL Nasal spray contributes to increased moisture and cleaner mucous membranes in upper respiratory tract so that conditions for infection are impaired, as well as the degree of irritation and inflammation upon colds is reduced. A secondary gain to reduced incidence of cold symptoms is that sickness absence is reduced among SAS attendants.

Production of VIIRAL Nasal Spray. VIIRAL Nasal Spray is manufactured by the Norwegian company Pharmatech AS; Vallehellene 4; 1664 Rolvsoy. VIIRAL Nasal Spray is prepared with Neu5Ac in a 0.9% NaCl aqueous solution. The spray box is a standard spray containing a volume of 20 ml. A spray bottle contains 150 mg sialic acid/Neu5Ac per 20 mL, i.e. 7.5 mg/ml. Pure Neu5Ac delivered by SigmaAldrich is used as sialic acid ingredient.

Information for Neu5Ac:

CAS Number: 131--48--6

Empirical formula: $C_{11}H_{19}NO_9$

Molecular Weight: 309.27

White powder, mp 185 to −187 degrees C.

Easily soluble in water

Production of placebo. Placebo product is manufactured in the same way as VIIRAL spray with Neu5Ac—but without Neu5Ac added, i.e. 0.9% NaCl in aqueous solution. All spray bottles in the study are labeled so that participants cannot identify the content.

Durability VIIRAL Nasal Spray. Durability of VIIRAL Nasal Spray is based on the durability of Neu5Ac in aqueous solution guaranteed from supplier.

Figure 3:
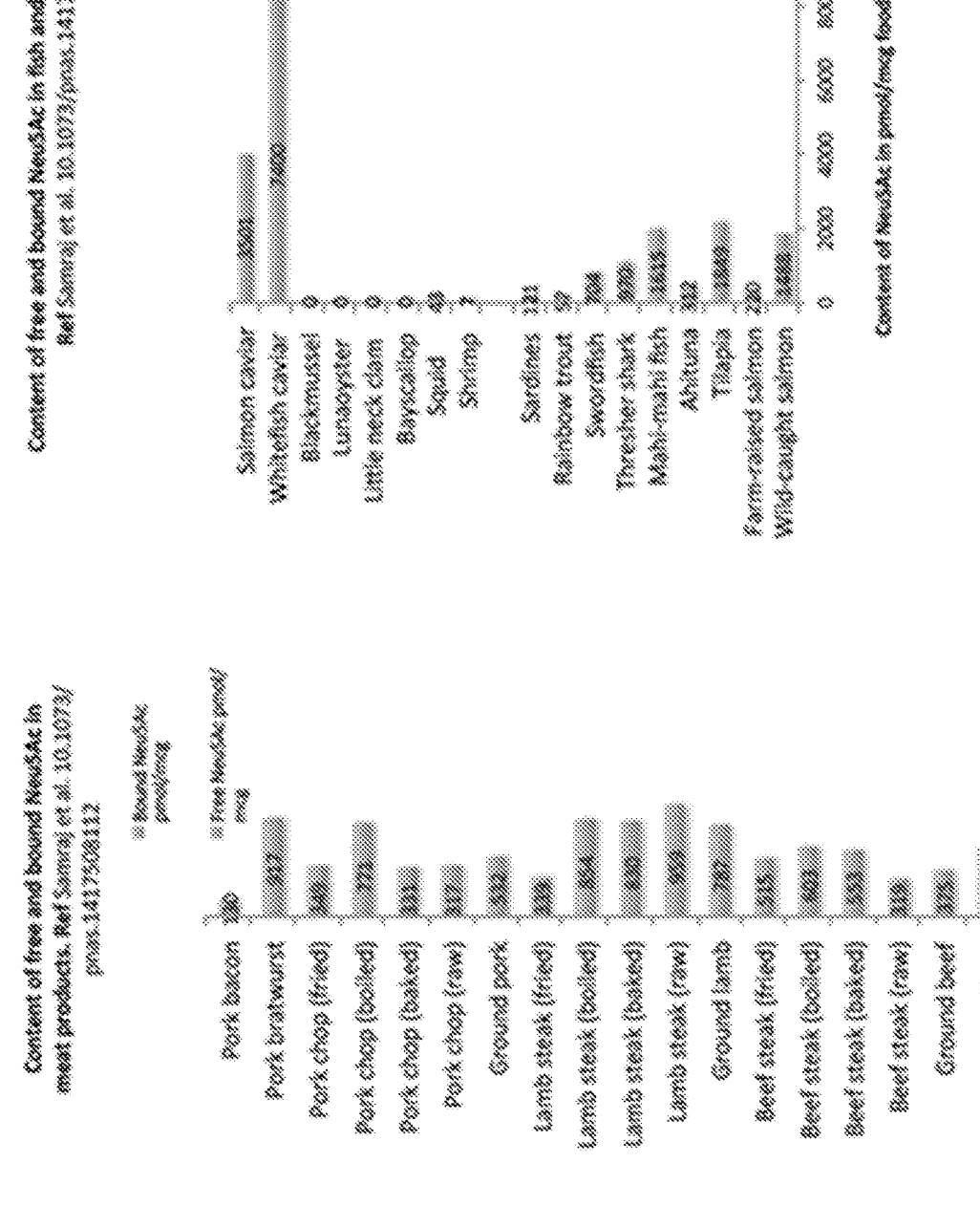
FIG. 3 shows Neu5Ac content in common foods: Meat, fish and seafood.
Figure 4:
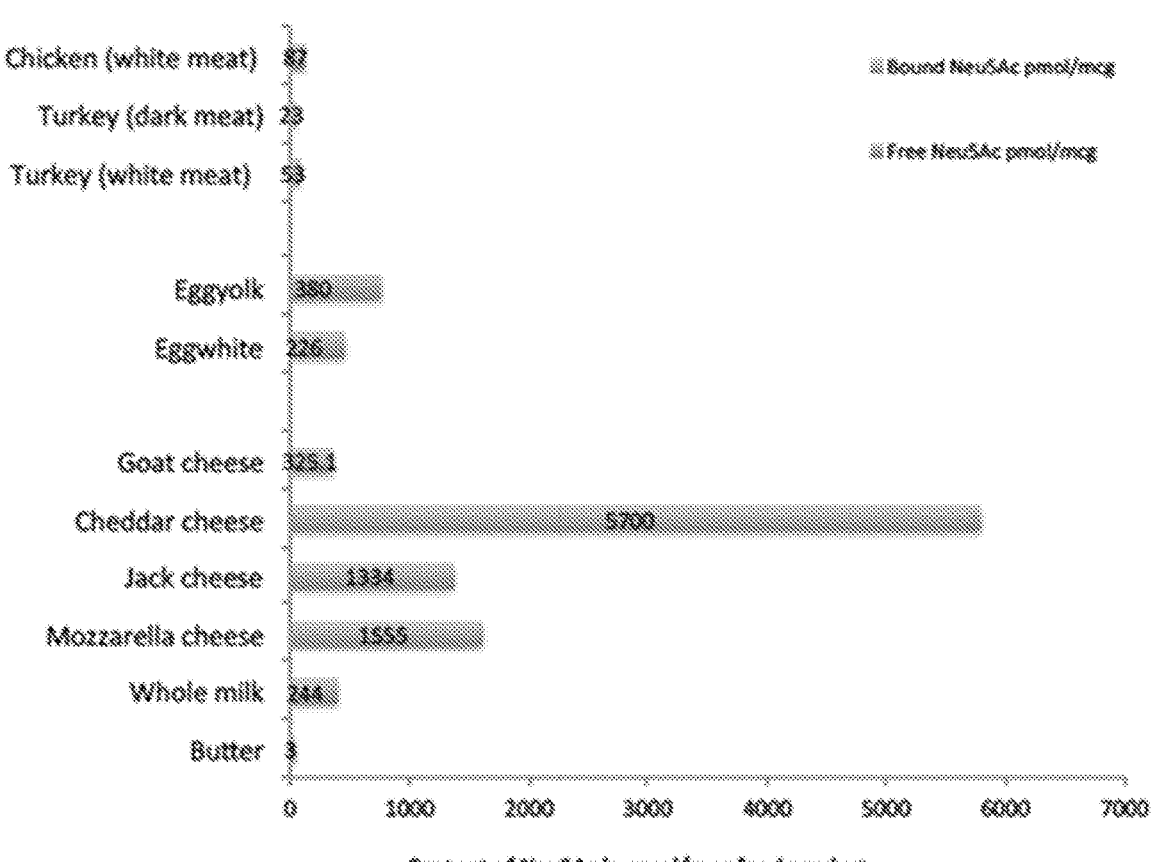
FIG. 4 shows Neu5Ac content—in picomol/micrograms product—in poultry and dairy products.

Neu5Ac is a naturally occurring component in food—that is, the sialic acid is a natural product. FIG. 3 and FIG. 4 show the content (in picomol/microgram food) of Neu5Ac in analyzed foods. Fruits and vegetables (those analyzed: carrot, cucumber, salad, tomato, potato, lemon, lime, olive oil, tofu, orange, banana, strawberry, peach, apple) do not contain sialic acids 13.

From FIG. 3 and FIG. 4 it appears that the vast majority of people with normal diets regularly consume significant amounts of Neu5Ac. FIG. 3 and FIG. 4 indicate amounts of Neu5Ac in picomol/microgram product—all values are therefore comparable.

FIG. 3 shows that meat products may vary slightly in the content of Neu5Ac based on preparation method (raw, cooked, fried etc)—however, the differences are not very large for lamb and cattle meat. For pigs, FIG. 3 shows that in this study there is more Neu5Ac in boiled meat and pork pork sausage other than pork cooked in different ways. Shellfish and other seafood show little or low content of Neu5Ac, while some types of fish and especially caviar/fish eggs contain a lot of Neu5Ac.

Figure 5:
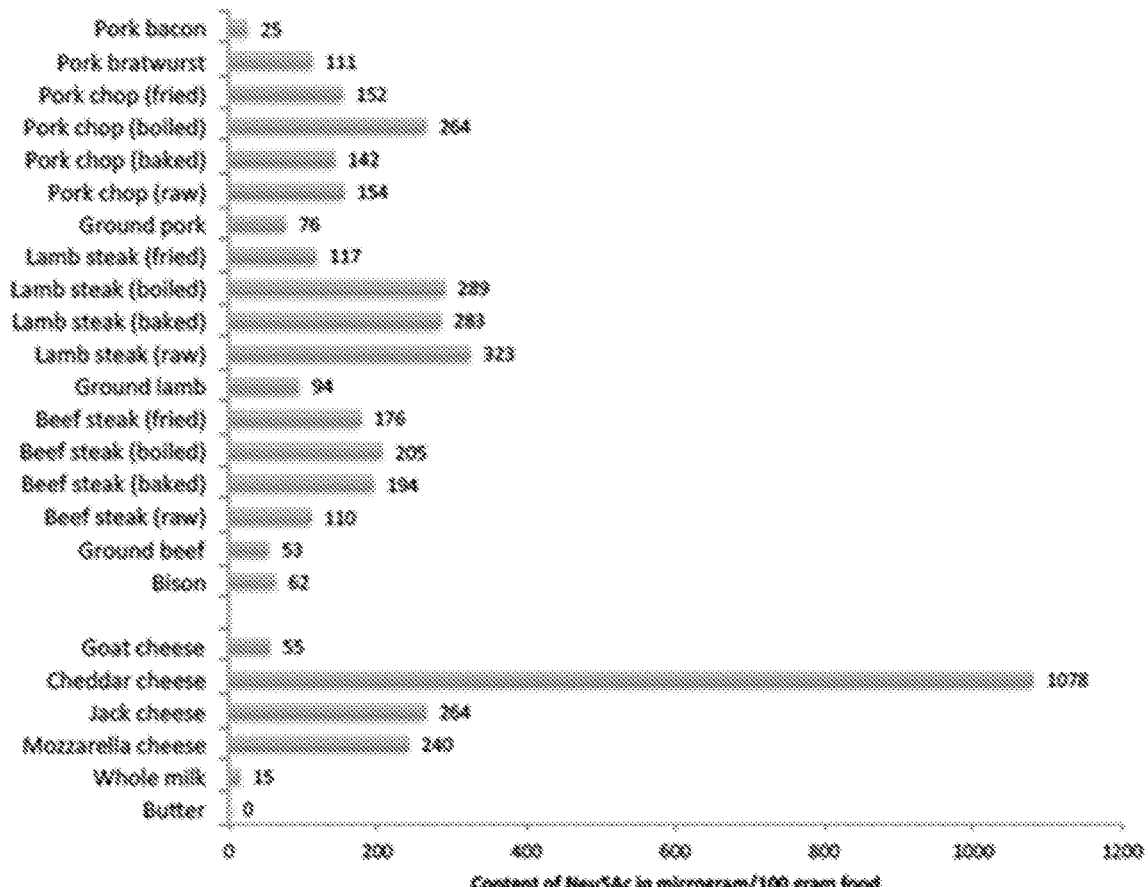
FIG. 5 shows Neu5Ac content in micrograms/100 grams of food.

FIG. 4 shows further content of Neu5Ac—in bound/conjugated form in a variety of foods (blue portion of column) in poultry and dairy products shown in picomol/microgram food. As shown, cheddar cheese contains the largest amount of Neu5Ac—again most conjugated Neu5Ac (blue column). Based on data described in FIGS. 3 and 4, the total content of Neu5Ac is calculated in the diet. Data is shown in FIG. 5 below. Therefore, with a normal diet of meat, fish and dairy products, relatively large amount of Neu5Ac are consumed daily.

The figures show that at a normal diet consisting of meat, fish, seafood and dairy products we consume significant amount of Neu5Ac daily.

Toxicity. The toxicity of Neu5Ac has been tested according to the standard test panel for oral tolerability and fertility 14 and for mutagenicity and genotoxisitet 15. No toxic effects have been detected. NOAEL for Neu5Ac is determined in rats to be 974 mg/kg body weight/day.

Based on toxicity data, content in common foods, quick excretion and desired concentration of Neu5Ac in VIIRAL Nasal Spray, as well as the above pilot, the quality assurance study concludes that it is safe to administer the product in this study.

Study design. The study is presented as a blinded, placebo controlled randomized study. Information about the study is prepared and sent to all participants.

Test Period 1:

Test Group A:

Target: 70-80 people using VIIRAL spray (150 mg Sialic acid/20 mL)—total exposure 9.2 mg/day for 4 weeks.

Test Group B:

Target: 70-80 people taking placebo spray exposure 0 mg/day for 4 weeks.

Delivery of spray boxes. Participants are given blinded spray boxes randomly marked with box number. All the boxes are weighed before extradition. 100% of the products (2 bottles of VIIRAL Nasal Spray) are delivered at the start of the study. Used spray boxes should not be discarded, but submitted to a student-based institution. Personnel responsible for the study collect all the spray boxes after use for inspection to ensure good compliance instructions.

Test Period 2:

The schedule for test period 2 is identical to test period 1.

Test group C:

Target: 70-80 people using VIIRAL spray (150 mg Sialic acid/20 mL)—total exposure 9.2 mg/day for 4 weeks.

Test group D:

Target: 70-80 people taking placebo spray exposure 0 mg/day for 4 weeks.

Inclusion and Exclusion Criteria. Inclusion:

From 18 years and upwards—both sexes

Employees in SAS as cabin crew

Exclusion:

Asthmatics

Respiratory allergies

Chronic lung disease

Persons who are on medication for chronic diseases & cancer patients

Individuals who have been vaccinated for the last six to twelve months.

Pregnant

VIIRAL Nasal Spray—dose and daily use. VIIRAL Nasal Spray is designed and should be used as other common nasal sprayers, for example 0.9% saline sprayers—both for those who receive spray containing Neu5Ac and Those who get placebo spray. Each Neu5Ac spray bottle contains 150 mg of sialic acid per 20 mL. Each spray bottle gives an average of 130 "showers", and each test person sprays each nostrils 2×2 times daily—primarily every morning and every evening, i.e. 8 sprays daily. This means that the test subjects are on average exposed to 9.2 mg sialic acid/Neu5Ac per day. (assumed intake of prescribed dosage) The dose is chosen based on the safety assessment that has been made and expected about results.

If desired, participants can take the 2×4 sprays (4 in each nostrils) spread throughout the day in other ways as long as the total amount becomes 8 sprays during one day. The times are entered in the reporting form.

The study period. The test subjects use the nasal spray as described for 4 weeks.

Reporting and information obtained. Observations are recorded electronically once a week (primarily on the same day each week) via a specially crafted computer software (an app) that can be downloaded to tablets or on a mobile phone. The computer program/app is made by the Norwegian companies eStep. Data is stored on the institution's server. Information about condition/reaction/response to the use of spray is spelled out in a form which uses a VAS scale.

The scale used ranges from 0 to 10 for reporting. The number 0 indicates no change, 10 indicates the maximum good effect for each parameter. Participants are encouraged to use the full scale. The computer program/"app" also has space to enter comments. Password Login Required.

Data is automatically processed on the company's website.

Observation Indicators. As observational indicators in the study, the following are used:

The number of nasal sprays that are used and answered all questions (Compliance)

General condition throughout the test period: An indication of whether the test subject is has a cold or other respiratory problems—and potential changes general state during the test period General feeling of moisture after using VIIRAL Nasal Spray General feeling of opening of the nose or after use of VIIRAL Nasal Spray The experience of reduced, no change or increased absenteeism during the test period as compared to before the test period.

Each day participants also consider their own health—focusing on condition of the upper airways.

Access to data. Collected data (see above) automatically enters the company's password-protected website. The responsible person has access to anonymous data.

Statistical methods. Standard statistical methods are used for data processing, preferably lifetime analyzes.

Based on the pilot study, a drop off of about 10% is contemplated. With 80 individuals per protocol, we estimate that we have strength to detectable approximately 20% difference between active treatment and placebo.

Example 3

SAS (Scandinavian Airline System) has—over many years—experienced at high percent of sick-leave among their cabin personnel. Mid 2017 it was established a contact between Viiral AS and SAS—including both the HR and the health care department in the company. One agreed to design a clinical test with Viiral Nasal Spray—testing the hypothesis if use of the product could reduce the number of "sick-leave days" among the SAS cabin personnel employees.

The study material (placebo and active Viiral Nasal Spray) were handed out by SAS at Gardemoen Airport in a double-blinded setup. Neither the study participant nor the SAS-personnel handling out the test-substance knew if compound A or B were active substance or placebo. The study was run in 4 weeks.

Study compound—Viiral Nasal Spray and Placebo. Viiral Nasal Spray (A) contained neuraminic acid, 1 mg/ml dissolved in isotonic (0.9%) saltwater (NaCl), pH 3.0. Each Spray bottle contained 20 mL, equal to 140 "dosages". The placebo Nasal Spray (B) contained isotonic (0.9%) saltwater (NaCl). Each Spray bottle contained 20 mL, equal to 140 "dosages". Using 2 double-spray's per nose-bore twice a day (8 sprays per day), each person should have 8×28=224 sprays during the 4-weeks test period; meaning 2 spray bottles per test person.

Study design and questions in the study protocol. The study was designed as a double blinded, randomized clinical trial. The study compounds (A and B) were handed out by SAS-personnel that did not know which of the two compounds (A or B) that represented the "active" compound—Viiral Nasal Spray. The placebo-compound (B) contained 0.9% saltwater—that in itself is known to reduce "dryness" in the nose and through that reduce risks for development of rhinitis/irritations in the upper respiratory tract.

The placebo study compound (B) was a little delayed in delivery to the SAS-site for handling out study—substance. This explains the "imbalance" in the number of recruited individuals in the A and B-group.

The study protocol included 6 questions—that should be answered after 1, 2, 3 and 4 weeks (the 6 questions should therefore be answered 4 times).

1. Have you taken the 2×4 spray dosages daily the last week?
2. Do you experience increased "wetness" in the nose?
3. Do you experience a more "open" nose?
4. Have you experienced more dryness, cold or other problems the last week?
5. Have you experienced more energy—associated with use of the nose-spray—the last week?
6. Have you stayed home from work due to diseases in the upper airway the last week? In case yes, how many days?

Study Results

Participation and Compliance (Question 1)

In total 127 individuals were recruited to the study, 78 to the active group (A) and 49 to the placebo-group (B).

Each individual should answer 5 questionnaires, meaning that answers of 508 questionnaires represent 100%.

In total 445 questionnaires (87.6%) were returned completed; 271 in the active group (A) and 174 in the placebo-group (B).

In total 68 individuals from the Viiral-group (A) and 43 individuals from the placebo-group (B) full-filled the 4-week test-period, representing a compliance of 86%.

For the question related to daily intake of 2×4 dosages—the compliance for the total group was 88%.

The individuals that did not fulfill the 4 weeks test period will (later) be described in a special table.

Wetness in the Nose (Question 2)

For the active-group (A) the improvements were experienced relatively after 1, 2, 3 and 4 weeks as 1,15; 1,46; 1,59 and 1,42 respectively.

For the placebo-group (B) the improvements were experienced relatively after 1, 2, 3 and 4 weeks as 1,30; 1,40; 1,27 and 1,40 respectively.

In conclusion: the experience of "a slightly better wetness" in the nose is described in both the active and the placebo-group of test persons; with a slightly better experience in the active ingredient group (A). However, 54% of the participants in the active group (A) experienced more wetness in the nose.

Nose Opening (Question 3)

Going through the individual comments to this question, it is recognized inconsistent data between the experience of "open nose" and "wetness" in the nose membrane.

For the active group (A) the numbers after 1, 2, 3 and 4 weeks are respectively: 1,15; 1,14; 1,23 and 1,17, For the placebo-group (B) the numbers are 1,20, 1,43, 1,02 and 1,2, In conclusion—there are small differences from the start-point of the study in both groups. If any different, the observations are in favor of the placebo-group (B). In total 50% of the participants in the active group (A) experienced more a more open nose.

The Incidence of "Tight Nose", Cold or Problems in the Upper Airways (Question 4)

This question will rank more problems with a higher number than less problems/improved situation. The test-persons have misunderstood this "changed" logic—and the answers are therefore confusing. This can be seen in the individual comments—added to the answers. We have therefore decided not to evaluate the answers on question 4.

Do You Experience More Energy During the Test Period (Question 5)

For the active group (A) the numbers after week 1, 2, 3 and 4 were respectively 0,25; 0,42; 0,29 and 0,41.

For the placebo group (B) the numbers were 0,37; 0,60; 0,71 and 0,57—respectively.

In conclusion: Very small changes in both groups. 19% of the participants in group A experienced more energy in their daily life.

Have You been Away from Work—if Yes how Many Days—from Disease in Upper Airways (Question 6)

In the active group the numbers of sick days (for 68 persons) was 41 days for the whole 4 weeks period—representing 2.23% sick leave if one calculates 7 days working weeks; or 3.13% if one calculates out from 5 days working weeks.

In the placebo group the number of sick days (for 43 persons) were 63 days—representing 5.29% calculating a 7 days working week and 7.23% if one use a 5 days working week.

Main Conclusions:

1. The study—double blinded, randomized clinical trial—has been run in 127 individuals with an 88% compliance related to returning the required answers on test-questions and administration of the 8 daily spray dosages.
2. The main parameter of the study (question 6) was to evaluate if Viiral Nasal Spray can reduce the number of sick-days resulting in disability of the SAS cabin-personnel to go to work. The 4 weeks clinical trial has documented a reduction of more than 56.7% in sick-leave of the SAS-personnel group taking Viiral Nasal Spray, as compared to the personnel taking placebo. This means that there is 131% higher sick-leave in the placebo-group as compared to the Viiral-group in the 4-week test period (5.29% sick-leave in the placebo-group compared to 2.23% sick-leave in the Viiral group).
3. Further on the experience of a "better nose-quality" (question 2 and 5) was reported in more than 50% of the participants receiving the active product (A)—the Viiral Nasal Spray.

Example 4

The NANA nasal spray described in Example 3 has been administered to a number of other subjects in series of individual test cases. In all instances the daily dosages are described as above. The results of these cases may be summarized as follows.

1. In multiple cases older subjects with dripping noses note a significant reduction in dripping or a complete stop in dripping nose.
2. In multiple cases, subjects reported a reduction or cessation of snoring.
3. A 5 year old with chronically clogged nasal cavities is free from daily clogging and sores in the nose following use of the NANA nasal spray.

4. A young soccer player with chronic immune deficiency that received the NANA nasal spray was immediately restored to normal workout capacity. In the past he got sick with flu like symptoms more or less after every workout and game he participated in.

5. An immune deficient teenager with kidney disease started the NANA nose spray treatment. The subject's glomerulonephritis and protein uremia were greatly reduced following treatment.

Example 5

A daily dose of 3 grams NANA was administered to a 50 year old subject suffering from chronic herpes outbreaks which had occurred approximately every other week for 10 years. After starting the NANA treatment, the subject has not had a herpes outbreak for two months.

REFERENCES

1 Ronald L. Schnaars, Rita Gerardy-Schahn, and Herbert Hildebrandt: sialic Acids in the Brain: Gangliosides and Polysialic Acid Nervous System Development, Stability, Disease, and Regeneration. Physiol Rev. 2014 April; 94 (2): 461-518.doi: 10.1152/physrev.00033.2013

2 Norbert Sprenger and Peter I. Duncan: sialic Acid Utilization. 2012 American Society for Nutrition. Adv. Nutr. 3: 392S-397S, 2012; doi: 10.3945/an.111.001479.

3 Jennifer E. Stencel-Baerenwald, Kerstin Reiss, Dirk M. Reiter, Thilo Stehle, and Terence S. Dermody: The sweet spot: Defining virus-sialic acid interactions. Nat Rev Microbiol. 2014 November; 12 (11): 739-749. doi: 10.1038/nrmicro3346.

3 B Wang and J Brand-Miller: The role and potential of sialic acid in human nutrition. Review.

4 Ursula Neu, Johannes Bauer, and Thilo Stehle. Viruses and sialic Acids: Rules of Engagement. Curr Opin Struct Biol. 2011 October; 21 (5): 610-618. doi: 10.1016/j.sbi.2011.08.009.

5 Schalcter M: N-Acetylneuraminic Acid (Neu5Ac). www.glyconutritionforlife.org/Science_of_Glyconutrients/N-Acetylneuraminic Acid_(Neu5Ac) php 6 Ajit Varki, sialic acids in human health and disease. Trends Mol Med. 2008 August; 14 (8): 351-360. doi: 10.1016/j.molmed.2008.06.002.

7 Thilo Stehle, Zaigham M. Khan: Rules and Exceptions: sialic Acid Variants and Their Role in Determining Viral Tropism. Journal of Virology p. 7696-7699 July 2014 Volume 88 Number 14

8 Muriel Bardor, Dzung H. Nguyen, Sandra Diaz, and Ajit Varki: Mechanism of Uptake and Incorporation of the Non-human sialic acid N-Glycolylneuraminic Acid into Human Cells. J Biol Chem Vol. 280, No. 6, Issue of February 11, pp. 4228-4237, 2005

9 Newburg, D S: Do the binding properties of oligosaccharides in milk protect human infants from gastrointestinal bacteria?J. Nutr. 127: 980S-984S, 1997.

10 Heine, W; Wutzke, K D; Radke M. Sialic acid in breast milk and infant formula food. Monatsschr Kinderheilkd. 1993 December; 141 (12): 946 to −50.

11 Boehm, G and Stahl, B. Oligosaccharides in milk. J. Nutr 2007, vol 137, p 847S-849S 12 Martin-Sosa, S, Martin, M-J and Hueso, P: The Sialylated Fraction of Milk oligosaccharides Ice Partially Responsible for Binding two enterotoxigenic and Uropathogenic Escherichia coli Human Strains. J. Nutr. 132: 3067-3072, 2002

13 Samraj A N, Pearce O M, Liubli H, Crittenden A N, Bergfeld A K, Banda K, Gregg C J, Bingman A E, Secrest P, Diaz S L, Varki N M, Varki A.: A red meat-derived glycan promoter inflammation and cancer progression. Proc Natl Acad Sci US A. 2015 Jan. 13; 112 (2): 542 to −7. doi:10.1073/pnas.1417508112. Epub 2014 December 29.

14 GRAS Notice (GRN) No. 602 http://www.fda.gov/Food/IngredientsPackagingLabeling/GRAS/NoticeInventory/default.htm ORIGINAL SUBMISSION 15 Choi, S H, Baldin, N., Wagner, V O (21), Roy, S., Rose, J., Thosrud, B A, Pnothirath, P. & Rörigh, C H 2014. Safety evaluation of the human—identical milk monosaccharide sialic acid (N-acetyl-D-neuraminic acid) in Sprague—Dawley rats. Regul. Toxicol. Pharmacol., 70, 482 to −491.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for inhibiting or treating an upper respiratory tract viral infection of a human subject suffering from or at risk of such an infection, said method comprising: intranasally administering via a pump spray device an aqueous spray formulation consisting of N-acetylneuraminic acid (NANA) as the active agent in a dosage of from 0.1 to 5.0 mg of NANA and physiologically acceptable carriers or excipients selected from the group consisting of water, saline, vitamins, minerals, colorants, propellants, anti-oxidants, preservatives, fillers, emulsifiers, suspending agents, dispersing agents, wetting agents, iso-osmotic agents and thixotropic agents, to each nostril of the subject suffering from or at risk of said upper respiratory tract viral infection under conditions such that said upper respiratory tract infection is inhibited or treated; wherein the pH of the aqueous formulation is from 2.8 to 3.2 and wherein said upper respiratory tract infection is selected from the group consisting of common colds and rhinovirus infection.

2. The method of claim 1, wherein said aqueous formulation comprises from about 0.1 to about 10 mg/ml of NANA in an aqueous solution.

3. The method of claim 1, wherein the dosage of NANA is from about 0.1 to 1.0 mg NANA/nostril/day.

4. The method of claim 1, wherein said dosage of NANA is delivered in from 2 to 8 administrations per day.

5. The method of claim 1, wherein said formulation further comprises a thixotropic agent.

6. The method of claim 5, wherein said thixotropic agent is selected from the group consisting of fucoidans, alginates and chitosan.

7. The method of claim 1, wherein said formulation further comprises mannuronic acid at a w/w percent range of 0.01 to 2.0%.

* * * * *